US011235135B2

(12) United States Patent
Tsai

(10) Patent No.: US 11,235,135 B2
(45) Date of Patent: Feb. 1, 2022

(54) BODY-FLUID-AND-MEDICATION LEAK-PROOF AND CLOSED MEDICAL CONNECTOR

(71) Applicant: Hsi-Chin Tsai, New Taipei (TW)

(72) Inventor: Hsi-Chin Tsai, New Taipei (TW)

( * ) Notice: Subject to any disclaimer, the term of this patent is extended or adjusted under 35 U.S.C. 154(b) by 241 days.

(21) Appl. No.: 16/188,859

(22) Filed: Nov. 13, 2018

(65) Prior Publication Data

US 2019/0282797 A1 Sep. 19, 2019

(30) Foreign Application Priority Data

Mar. 19, 2018 (TW) .................................. 107109235

(51) Int. Cl.
| | | |
|---|---|---|
| *A61M 39/22* | (2006.01) | |
| *A61M 39/10* | (2006.01) | |
| *A61J 1/20* | (2006.01) | |
| *A61M 39/26* | (2006.01) | |

(52) U.S. Cl.
CPC ............ *A61M 39/22* (2013.01); *A61J 1/2037* (2015.05); *A61J 1/2096* (2013.01); *A61M 39/10* (2013.01); *A61J 1/201* (2015.05); *A61J 1/2089* (2013.01); *A61M 2039/267* (2013.01)

(58) Field of Classification Search
CPC .... A61M 2039/2433; A61M 2039/267; A61M 39/10; A61M 39/22; A61J 1/201; A61J 1/2037; A61J 1/2089; A61J 1/2096
See application file for complete search history.

(56) References Cited

U.S. PATENT DOCUMENTS

| | | | |
|---|---|---|---|
| 5,509,433 A | 4/1996 | Paradis | |
| 7,981,090 B2 * | 7/2011 | Plishka | ............... A61M 39/045 |
| | | | 604/249 |
| 7,998,134 B2 | 8/2011 | Fangrow et al. | |
| 8,425,489 B2 | 4/2013 | Hofmann et al. | |
| 8,545,476 B2 | 10/2013 | Ariagno et al. | |
| 9,039,047 B2 | 5/2015 | Imai | |
| 9,114,242 B2 | 8/2015 | Fangrow et al. | |

(Continued)

FOREIGN PATENT DOCUMENTS

| | | |
|---|---|---|
| CN | 102015014 A | 4/2011 |
| CN | 102421465 A | 4/2012 |

(Continued)

*Primary Examiner* — Quynh-Nhu H. Vu
(74) *Attorney, Agent, or Firm* — Alan D. Kamrath; Karin L. Williams; Mayer & Williams PC

(57) ABSTRACT

A body-fluid-and-medication leak-proof and closed medical connector has a first connecting assembly and a second connecting assembly. The first connecting assembly has a first sleeve and a first resilient valve. The first resilient valve tends to seal a first opening of the first sleeve. The second connecting assembly has a second sleeve and a second resilient valve. The second resilient valve tends to seal a second opening of the second sleeve. The two resilient valves can avoid leakage of the medication remaining in an injector and a vial, or remaining in a fluid infusion tube and a catheter. The two resilient valves also can seal in two directions to avoid leakage during connecting or separating the two connecting assemblies after supplying medication. Therefore, the transfer of the medication is more hygienic and safe, and the waste of medical resources is effectively reduced.

6 Claims, 18 Drawing Sheets

(56) References Cited

U.S. PATENT DOCUMENTS

| | | |
|---|---|---|
| 9,126,028 B2 | 9/2015 | Fangrow et al. |
| 9,126,029 B2 | 9/2015 | Fangrow et al. |
| 9,358,181 B2 | 6/2016 | Ariagno et al. |
| 9,724,504 B2 | 8/2017 | Fangrow, Jr. et al. |
| 9,925,365 B1 * | 3/2018 | Ryan ................. A61M 39/1011 |
| 10,022,301 B2 | 7/2018 | Ivosevic et al. |
| 10,086,188 B2 | 10/2018 | Fangrow |
| 10,238,858 B2 | 3/2019 | Ueda et al. |
| 10,391,293 B2 | 8/2019 | Fangrow |
| 10,398,887 B2 | 9/2019 | Fangrow, Jr. et al. |
| 10,537,495 B2 | 1/2020 | Ivosevic et al. |
| 10,799,692 B2 | 10/2020 | Fangrow |
| 10,918,851 B2 | 2/2021 | Guala |
| 10,925,807 B2 | 2/2021 | Ivosevic et al. |
| 10,945,650 B2 | 3/2021 | Jeffrey |
| 2003/0032940 A1 * | 2/2003 | Doyle ................. A61M 39/045 604/533 |
| 2008/0048144 A1 | 2/2008 | Lynn |
| 2011/0015566 A1 * | 1/2011 | Pan ....................... A61M 39/26 604/68 |
| 2014/0323988 A1 | 10/2014 | Magnani et al. |
| 2016/0317798 A1 | 11/2016 | Lopez et al. |
| 2017/0119965 A1 | 5/2017 | Butterfield |
| 2017/0326350 A1 | 11/2017 | Rogier |
| 2019/0184152 A1 | 6/2019 | Kakinoki |

FOREIGN PATENT DOCUMENTS

| | | |
|---|---|---|
| CN | 202605411 U | 12/2012 |
| CN | 103153260 A | 6/2013 |
| CN | 103961793 A | 8/2014 |
| CN | 104096283 A | 10/2014 |
| CN | 104203333 A | 12/2014 |
| CN | 105013076 A | 11/2015 |
| CN | 106163608 A | 11/2016 |
| CN | 106267545 A | 1/2017 |
| CN | 106421960 A | 2/2017 |
| CN | 205994799 U | 3/2017 |
| CN | 206026779 U | 3/2017 |
| CN | 206491796 U | 9/2017 |
| CN | 107595625 A | 1/2018 |
| CN | 107596496 A | 1/2018 |
| CN | 107626037 A | 1/2018 |
| CN | 107847728 A | 3/2018 |
| CN | 107847729 A | 3/2018 |
| TW | 201438780 A | 10/2014 |
| TW | 201615232 A | 5/2016 |
| WO | WO2016152016 A1 | 9/2016 |
| WO | WO2018056465 A1 | 3/2018 |

\* cited by examiner

BODY-FLUID-AND-MEDICATION LEAK-PROOF AND CLOSED MEDICAL CONNECTOR

BACKGROUND OF THE INVENTION

1. Field of the Invention

The present invention relates to a medical injector, and more particularly to a needleless medical connector for a vial or a catheter into a human body, and a needleless medical connector for a needle of an injector or a fluid infusion tube.

2. Description of the Prior Arts

A medical injector is used to inject medication into a patient. A conventional medical injector comprises a needle, which can inject the medication inside the injector into the patient. However, the needle is unsafe and may pierce another object and medical personnel may accidentally get stabbed by the needle. Accordingly, a needleless medical injector without using a needle has been developed. During supply of medication, a needleless medical injector is connected to a vial through a connector, so that the injector can extract the medication in the vial.

An ordinary connector comprises a first connecting assembly and a second connecting assembly. The first connecting assembly is used to connect an injector or a fluid infusion tube. The second connecting assembly is used to connect a vial or a catheter. The first connecting assembly and the second connecting assembly are connected to each other. The first connecting assembly comprises a resilient plug and an actuator. The resilient plug selectively blocks an opening of the first connecting assembly for connecting to the second connecting assembly. The actuator keeps abutting the resilient plug, and the actuator selectively protrudes out of the first connecting assembly. When the first connecting assembly and the second connecting assembly are connected to each other, the second connecting assembly abuts and pushes the actuator, and the actuator moves to push and move the resilient plug. So the resilient plug does not block the opening of the first connecting assembly, and the first connecting assembly communicates with the second connecting assembly.

However, when the above-mentioned connector is used, the first connecting assembly and the second connecting assembly are separated. During the separation of the first connecting assembly and the second connecting assembly, a gap between the second connecting assembly and the first connecting assembly is getting larger, but the second connecting assembly still abuts the actuator, such that the first connecting assembly is not closed yet, which makes the medication keep flowing into a space between the second connecting assembly and the first connecting assembly until the first connecting assembly and the second connecting assembly are fully separated and then the first connecting assembly and the second connecting assembly are respectively closed. Therefore, some medication may remain in the opening of the first connecting assembly and an opening of the second connecting assembly. Particularly during the transfer of the medication, the first connecting assembly and the second connecting assembly may need to be separated temporarily, which may cause more medication to remain outside. The remaining medication may volatilize due to the contact with the air or may directly contact the human body, and the medication may deteriorate or the medication is harmful itself, which results in infection to the human body. In other words, the leaked and exposed medication is potentially dangerous for the user.

As a result, the conventional connector needs to be improved.

To overcome the shortcomings, the present invention provides a body-fluid-and-medication leak-proof and closed medical connector to mitigate or obviate the aforementioned problems.

SUMMARY OF THE INVENTION

The main objective of the present invention is to provide a body-fluid-and-medication leak-proof and closed medical connector to avoid some medication remaining on an outer surface of the needleless closed medical connector after used.

One of two ends of the body-fluid-and-medication leak-proof and closed medical connector is detachably connected to an injector or a fluid infusion tube, the other of the two ends of the body-fluid-and-medication leak-proof and closed medical connector is detachably connected to a vial or a catheter, thereby communicating between the injector and the vial, or communicating between the fluid infusion tube and the catheter. The body-fluid-and-medication leak-proof and closed medical connector comprises a first connecting assembly and a second connecting assembly.

The first connecting assembly is detachably connected to the injector or the fluid infusion tube, communicates with the injector or the fluid infusion tube, and comprises a first sleeve and a first resilient valve. The first sleeve has a first end, a second end, and a first channel. The first end is detachably connected to the injector or the fluid infusion tube. The first channel is formed through the first sleeve, extends from the first end of the first sleeve to the second end of the first sleeve, communicates with the injector or the fluid infusion tube, and forms a first opening in the second end of the first sleeve. The first resilient valve is mounted in the first channel and tends to seal the first opening.

The second connecting assembly is detachably connected to the vial or the catheter, communicates with the vial or the catheter, is detachably connected to the first connecting assembly, and comprises a second sleeve, a connecting portion, and a second resilient valve. The second sleeve has a first end, a second end, and a second channel. The first end is detachably connected to the vial or the catheter. The second end is detachably connected to the second end of the first sleeve. The second channel is formed through the second sleeve, extends from the first end of the second sleeve to the second end of the second sleeve, communicates with the vial or the catheter, and foil is a second opening in the second end of the second sleeve. The connecting portion is mounted in the second channel and has a closed end and at least one lateral hole. The at least one lateral hole is formed through a side wall of the connecting portion, communicates with an inner space of the connecting portion, and is disposed adjacent to the closed end of the connecting portion. The second resilient valve is mounted in the second channel, and tends to seal the second opening.

When the first connecting assembly and the second connecting assembly are connected to each other, the first sleeve abuts the second resilient valve to move the second resilient valve relative to the connecting portion to expose the at least one lateral hole of the connecting portion out of the second resilient valve. Simultaneously, the closed end of the connecting portion abuts the first resilient valve to open the first opening such that the first connecting assembly and the second connecting assembly communicate with each other.

The first resilient valve, which tends to seal the first opening of the first sleeve, in the first sleeve of the first connecting assembly can effectively avoid the leakage of the remaining medication in the first connecting assembly. Simultaneously, the second resilient valve, which tends to seal the second opening of the second sleeve, in the second sleeve of the second connecting assembly can effectively avoid the leakage of the remaining medication in the second connecting assembly. With the aforementioned structure, the needleless closed medical connector can effectively reduce the contact between the medication and the air, and also reduce the medication remaining on outer surfaces of the first connecting assembly and the second connecting assembly to avoid bacterial breeding. Therefore, the transfer of the medication is more hygienic and safe. In addition, by reducing the medication remaining outside of the vial, the user can draw less medication from the vial with precious chemotherapy medications, thereby effectively reducing waste of medical resources.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
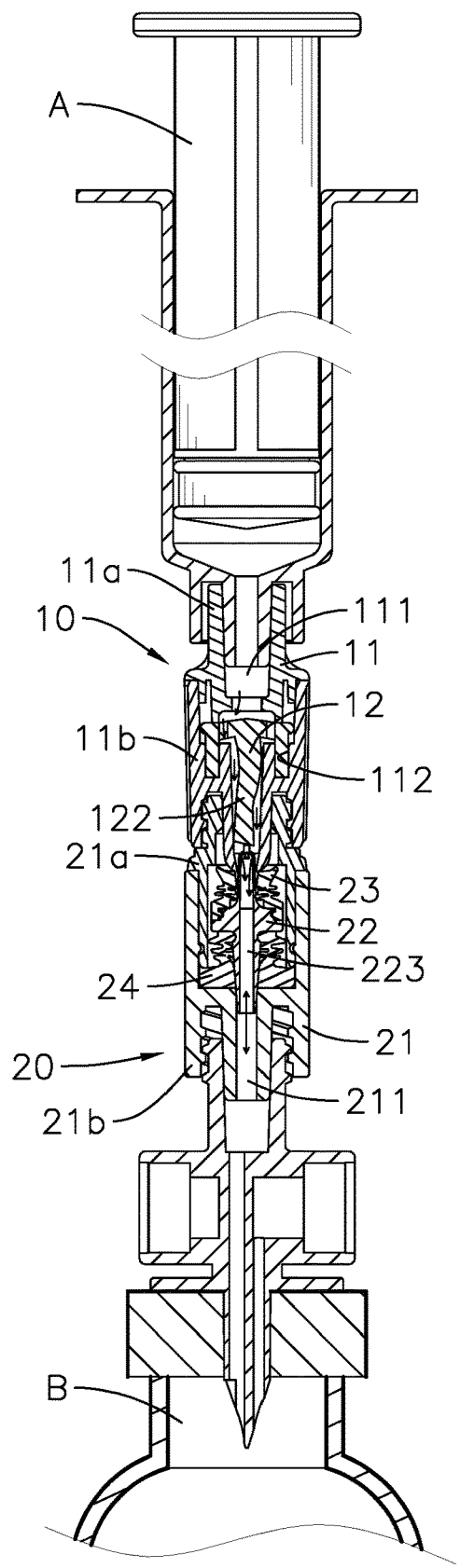
FIG. 1 is a front view in partial section of a first embodiment of a body-fluid-and-medication leak-proof and closed medical connector in accordance with the present invention, showing a first connecting assembly and a second connecting assembly connected with each other.
Figure 2:
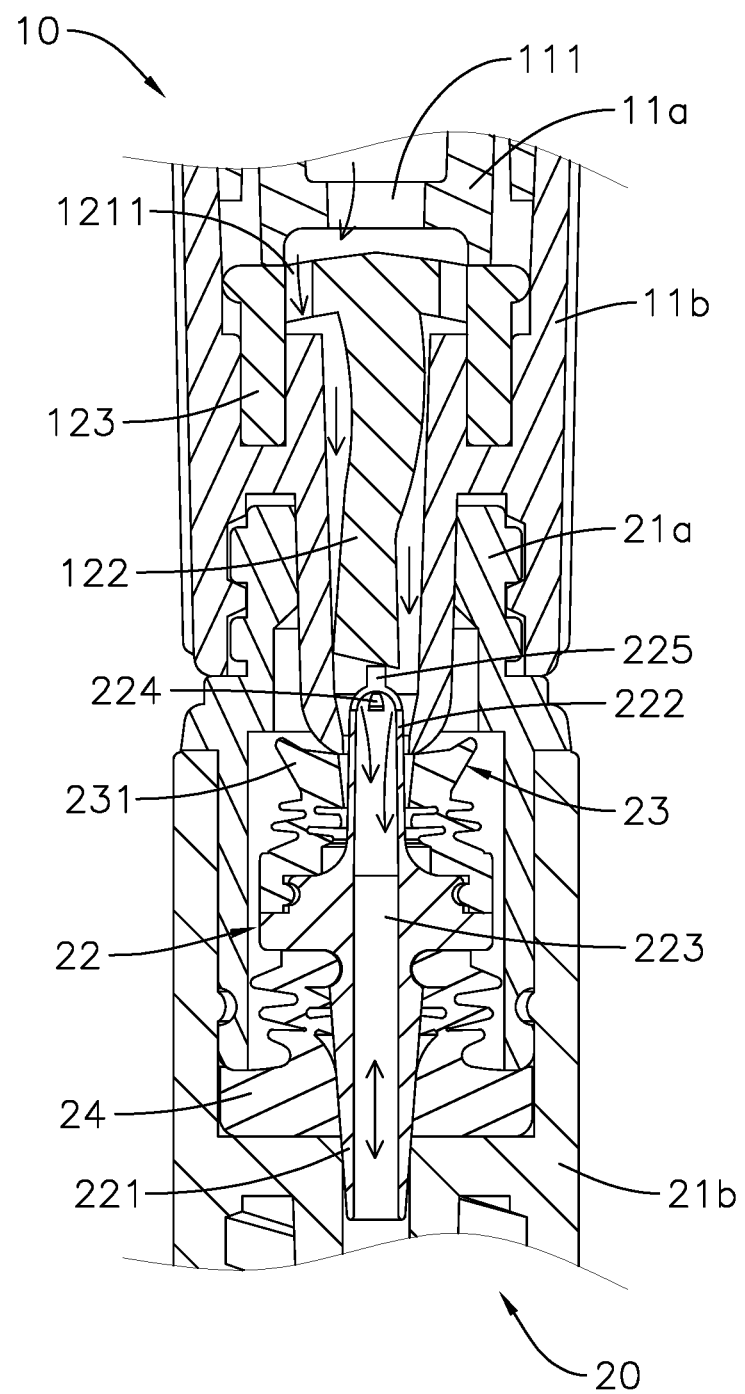
FIG. 2 is an enlarged view of FIG. 1.
Figure 3:
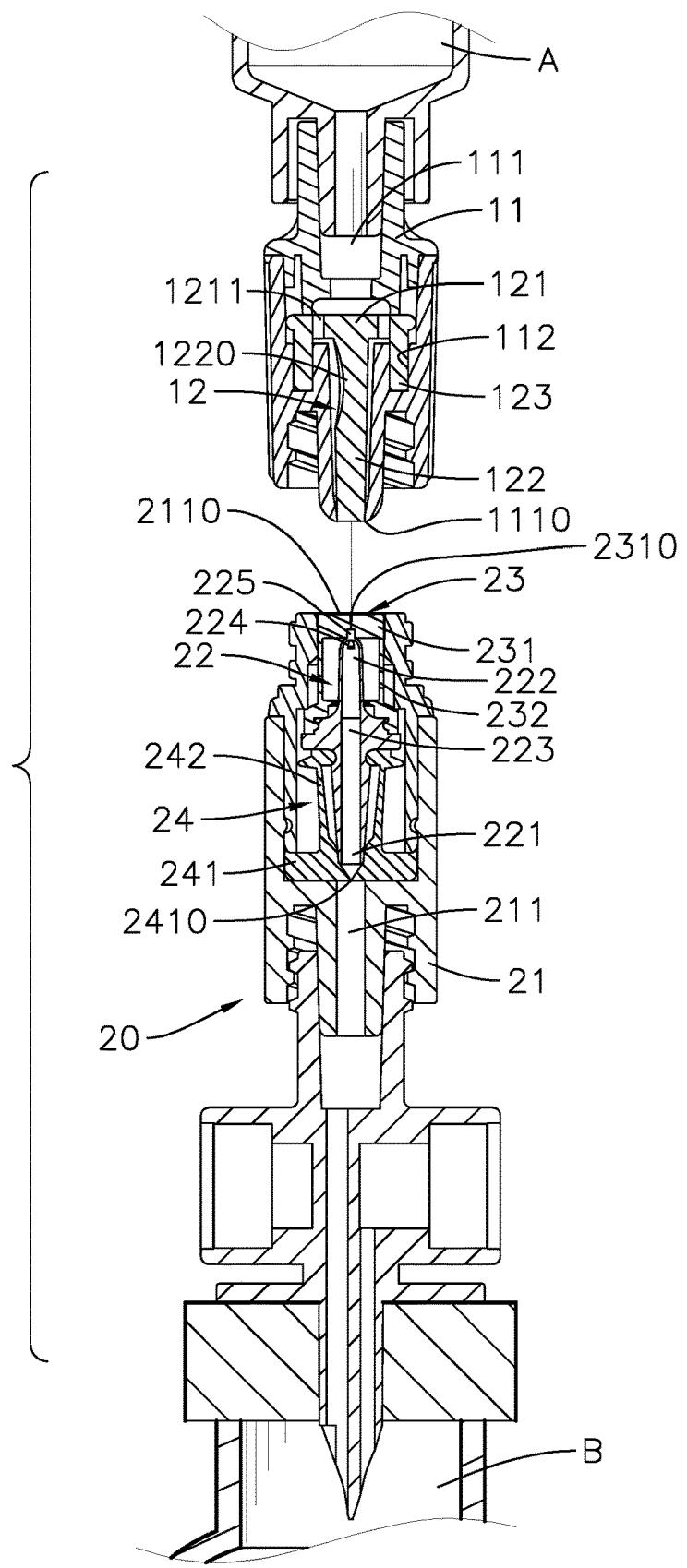
FIG. 3 is a front view in partial section of the body-fluid-and-medication leak-proof and closed medical connector in FIG. 1, showing the first connecting assembly and the second connecting assembly separating.
Figure 6:
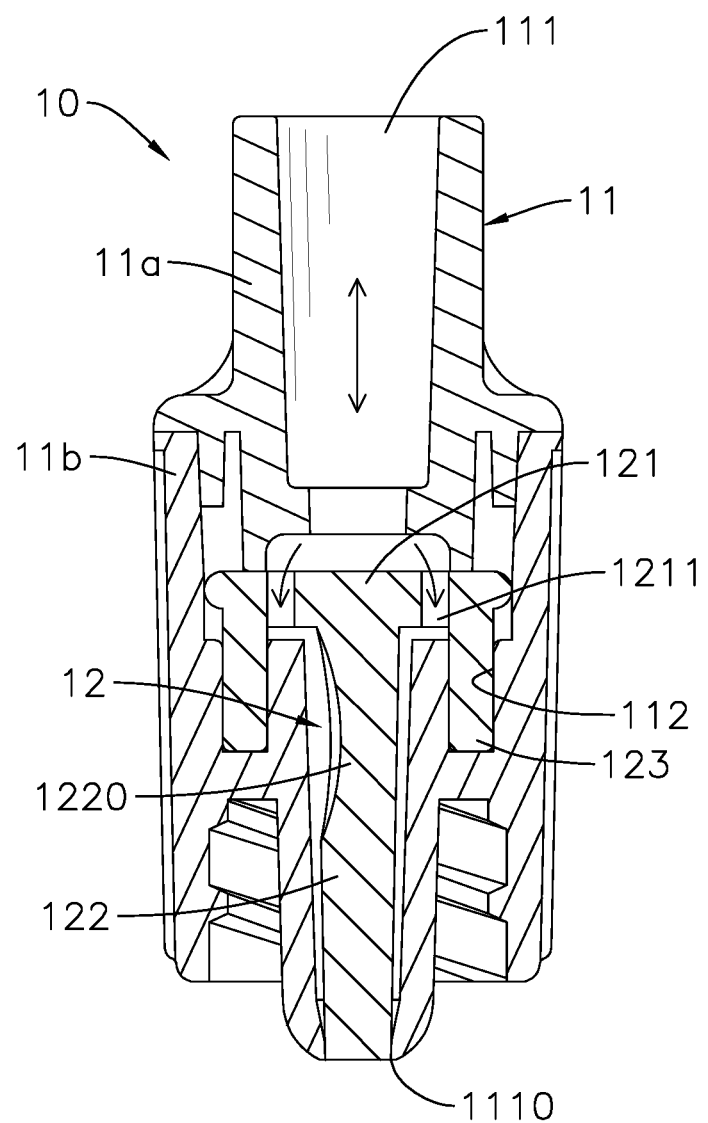

With reference to FIGS. 1, 2, and 6, a body-fluid-and-medication leak-proof and closed medical connector in accordance with the present invention has two ends. One of the two ends is detachably connected to an injector A, and the other end is detachably connected to a vial B, thereby communicating between the injector A and the vial B. The body-fluid-and-medication leak-proof and closed medical connector in accordance with the present invention further comprises a first connecting assembly 10 and a second connecting assembly 20.

The first connecting assembly 10 is detachably connected to the injector A and communicates with the injector A. The first connecting assembly 10 has a first sleeve 11 and a first resilient valve 12.

Figure 9:
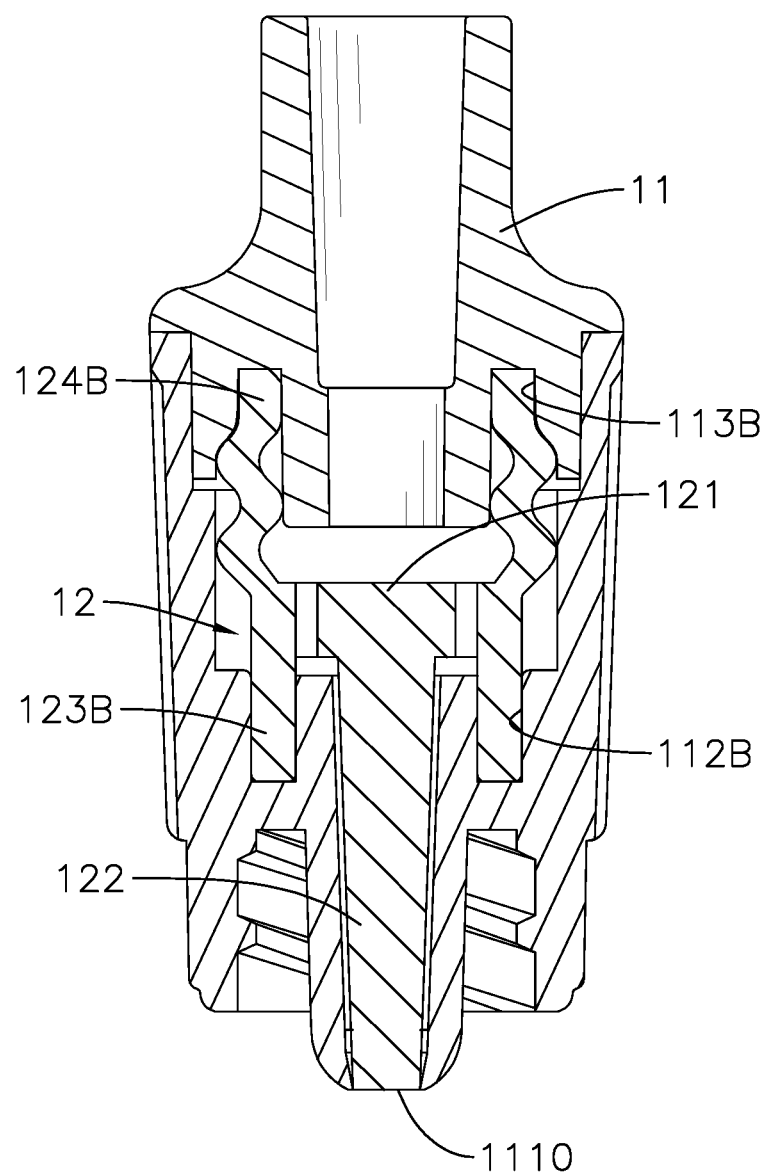
FIGS. 9 and 10 are front views in partial section of the first connecting assembly of a third embodiment of a body-fluid-and-medication leak-proof and closed medical connector in accordance with the present invention.

The first sleeve 11 has a first end, a second end, and a first channel 111, and the first sleeve 11 optionally has a positioning recess 112 and/or an accommodating recess 113B as shown in FIG. 9 and in the third preferred embodiment. The first end is detachably connected to the injector A, and may be connected to the injector A by threads or engagement. The first channel 111 is formed through the first sleeve 11, extends from the first end to the second end, and communicates with the injector A. The first channel 111 forms a first opening 1110 in the second end. The positioning recess 112 is formed in the first sleeve 11, and surrounds and communicates with the first channel 111. In a preferred embodiment, the first sleeve 11 has a first sleeve unit 11a and a second sleeve unit 11b. The first sleeve unit 11a is detachably connected to the injector A. The second sleeve unit 11b is mounted securely on the first sleeve unit 11a. In other words, the first sleeve unit 11a forms the first end of the first sleeve 11, and the second sleeve unit 11b forms the second end of the first sleeve 11. The first channel 111 is formed through the first sleeve unit 11a and the second sleeve unit 11b, and the first opening 1110 is formed in the second sleeve unit 11b.

The first resilient valve 12 is mounted in the first channel 111, and tends to seal the first opening 1110. The first resilient valve 12 has a plated portion 121 and a plug post 122, and optionally has a positioning portion 123 and a flexing portion 124B as shown in FIG. 9 and in the third preferred embodiment. The plated portion 121 is clamped between the first sleeve unit 11a and the second sleeve unit 11b, and thus the first resilient valve 12 is fixed in position. The plated portion 121 may be made of a resilient material, and has multiple communicating holes 1211 to communicate between both sides of the first channel 111. The plug post 122 is mounted securely on the plated portion 121, and is mounted in the second sleeve unit 11b to selectively seal the first opening 1110. To be specific, the plug post 122 is made of a resilient material, and optionally has a necked portion 1220. The necked portion 1220 is a portion that has smaller sectional area relative to other portions of the plug post 122, thereby enlarging the bending of the plug post 122 when receiving an external force, which ensures the first opening 1110 will be opened when the plug post 122 is bent. In a preferred embodiment, the necked portion 1220 has a notch formed in a side surface of the plug post 122, but the necked portion 1220 may be formed in other shapes.

The specific embodiments of the first sleeve 11 and the first resilient valve 12 are as follows:

With reference to FIG. 6, in the first preferred embodiment, the second sleeve unit 11b of the first sleeve 11 has the positioning recess 112, and the first resilient valve 12 has the positioning portion 123. The positioning recess 112 not only surrounds the first channel 111m but also surrounds the plug post 122. The positioning recess 112 may be formed in an inner wall of the second sleeve unit 11b, and extends along a lengthwise direction of the first channel 111. The positioning portion 123 also surrounds the plug post 122, and has two ends. One of the two ends is connected to the plated portion 121, and the other end is positioned in the positioning recess 112. The positioning portion 123 keeps the first resilient valve 12 in a center of the first channel 111 after the first resilient valve 12 is bent.

Figure 7:
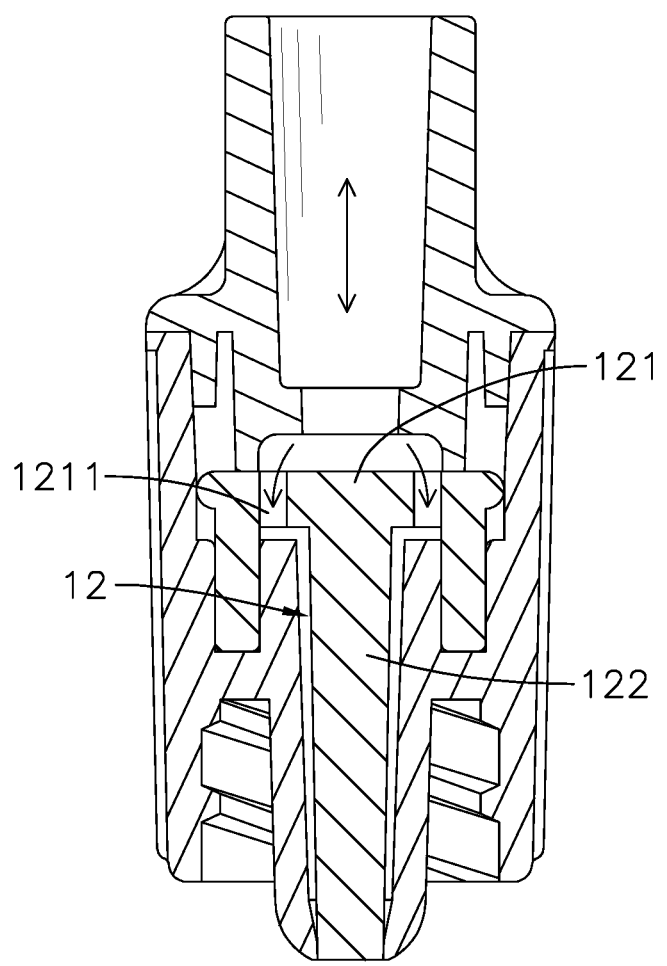
FIG. 7 is a front view in partial section of the first connecting assembly of another embodiment of a body-fluid-and-medication leak-proof and closed medical connector in accordance with the present invention.

In a preferred embodiment, the plug post 122 is made of a resilient material and has a necked portion 1220. The plug post 122 may be implemented without the necked portion 1220 as shown in FIG. 7. The necked portion 1220 may have a notch formed in the side surface of the plug post 122, and thus the necked portion 1220 is smaller in width than other portions of the plug post 122. Preferably, the notch of the necked portion 1220 is disposed adjacent to the plated portion 121. In a preferred embodiment, the positioning portion 123 is shaped as a sleeve and mounted securely in the positioning recess 112. However, in another preferred embodiment, the positioning portion 123 may be protruding ribs or protrusions, as long as the positioning portion 123 can be fixed in the positioning recess 112. Due to the first sleeve unit 11a and the second sleeve unit 11b clamping the plated portion 121, the positioning portion 123 mounted in the positioning recess 112, and the resilient plug post 122, the plug post 122 can open the first opening 1110 when receiving an external force and can be recovered to seal the first opening 1110 again when receiving no external force.

Figure 8:
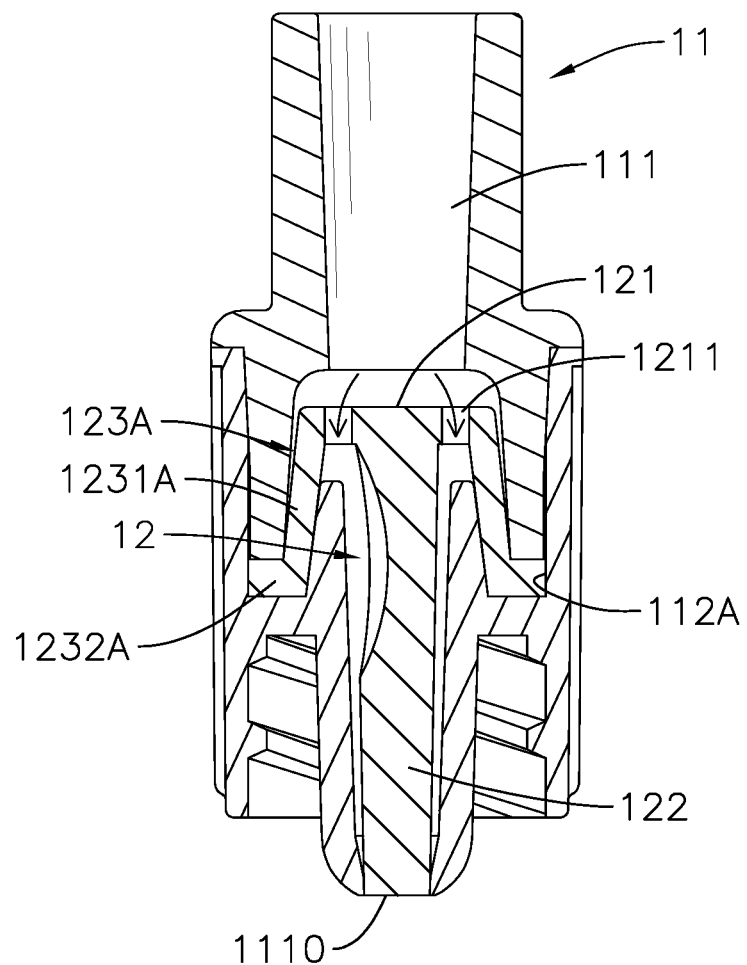
FIG. 8 is a front view in partial section of the first connecting assembly of a second embodiment of a body-fluid-and-medication leak-proof and closed medical connector in accordance with the present invention.

With reference to FIG. 8, in the second preferred embodiment, the first sleeve 11 also has the positioning recess 112A, and the first resilient valve 12 also has the positioning portion 123A. The positioning recess 112A is also formed in an inner wall of the first channel 111, but the positioning recess 112A extends along a direction perpendicular to the lengthwise direction of the first channel 111. The positioning portion 123A may have an extending wall 1231A and a protruding rib1232A. The extending wall 1231A may be shaped as a sleeve, and surrounds the plug post 122. One of two ends of the extending wall 1231A is connected to the plated portion 121. The protruding rib1232A extends from the other end of the extending wall 1231A along a direction perpendicular to the lengthwise direction of the first channel 111, so that the plated portion 121 can be mounted securely in the positioning recess 112A. Compared with the preferred embodiment without the extending wall 1231A, the second preferred embodiment with the extending wall 1231A can have the longer plug post 122, so that the bending of the plug post 122 is also larger, thereby ensuring the plug post 122 can open the first opening 1110 when bent.

Figure 10:
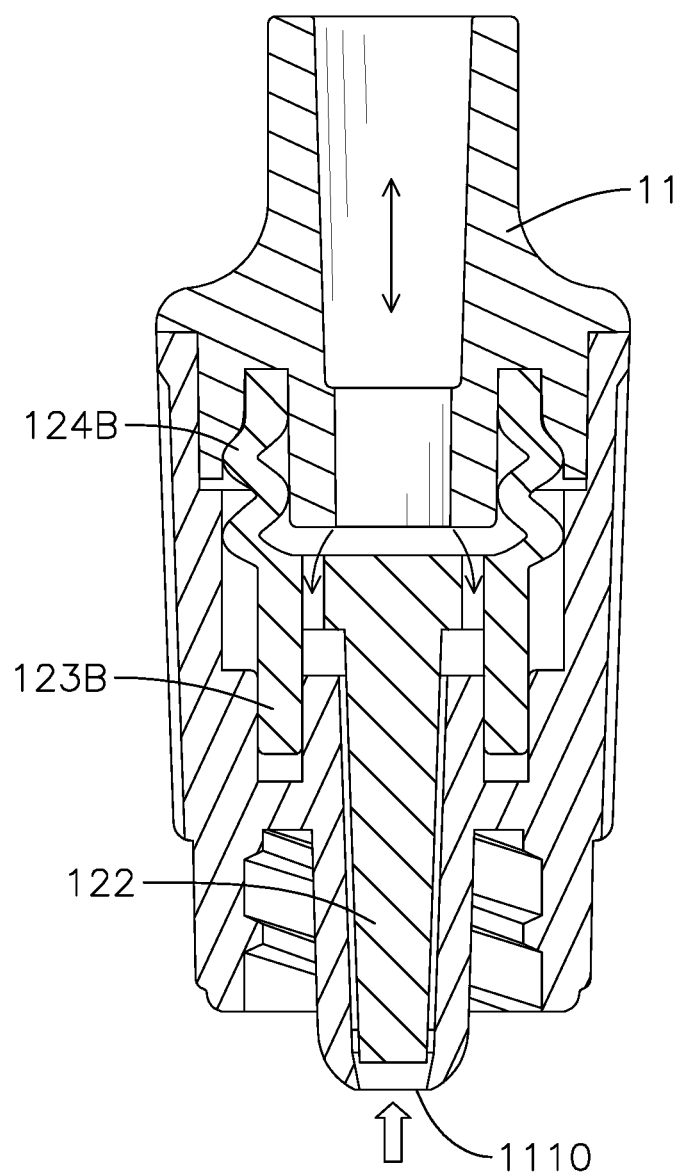

With reference to FIGS. 9 and 10, in the third preferred embodiment, the first sleeve 11 also has the positioning recess 112B but further has an accommodating recess 113B. The first resilient valve 12 also has the positioning portion 123B but further has a flexing portion 124B. The positioning recess 112B, the positioning portion 123B and the plug post 122 in the third preferred embodiment are similar to those in the first preferred embodiment, and thus are not repeated. The accommodating recess 113B surrounds the first channel 111 and communicates with the first channel 111. The accommodating recess 113B and the plug post 122 are disposed on both sides of the plated portion 121 respectively. One of two ends of the flexing portion 124B is connected to the plated portion 121, and the other end is mounted in the accommodating recess 113B. In a preferred embodiment, the plug post 122 may be made of a non-resilient material, and thus the first resilient valve 12 moves the plug post 122 by the deformation of the flexing portion 124B, thereby opening the first opening 1110. In another preferred embodiment, the first sleeve 11 may have the accommodating recess 113B only and without the positioning recess 112B. In the same way, the first resilient valve 12 has the flexing portion 124B only and does not have the positioning portion 123B.

Figure 11:
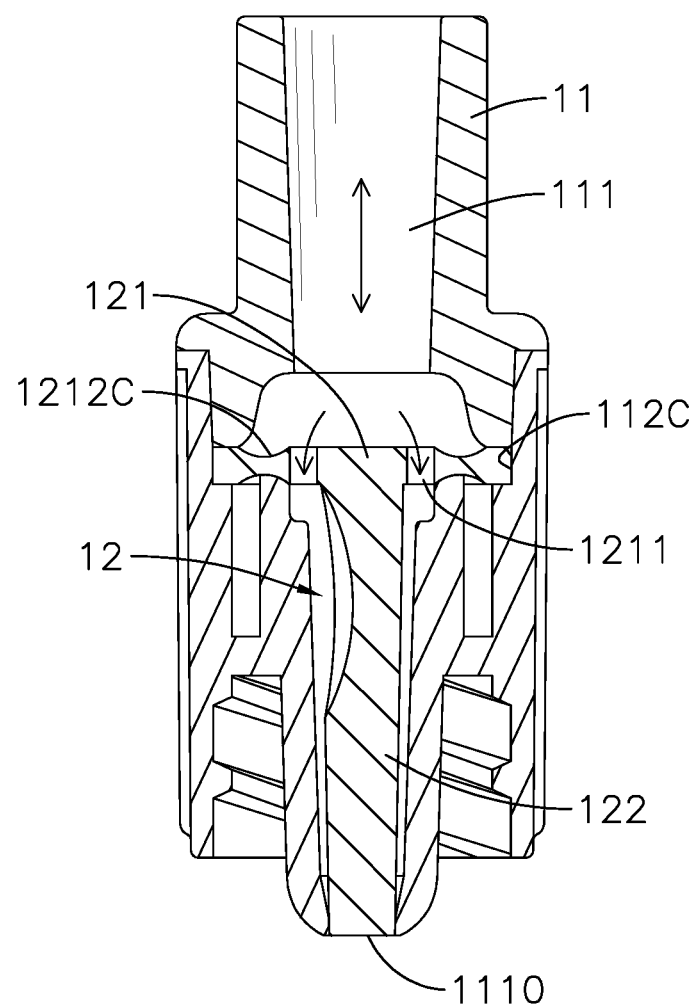
FIG. 11 is a front view in partial section of the first connecting assembly of a fourth embodiment of a body-fluid-and-medication leak-proof and closed medical connector in accordance with the present invention.

With reference to FIG. 11, in the fourth preferred embodiment, the first sleeve 11 also has the positioning recess 112C. The positioning recess 112C is formed in the inner wall of the first channel 111, and extends along a direction perpendicular to the lengthwise direction of the first channel 111. The first resilient valve 12 may be implemented without the positioning portion and the flexing portion, but the plated portion 121 further has at least one annular recess 1212C. To be specific, the plated portion 121 is mounted securely in the positioning recess 112C, and has two annular recesses 1212C respectively formed in a top surface and a bottom surface of the plated portion 121 respectively. Furthermore, the plated portion 121 is made of a resilient material. Thus, when the plug post 122 receives an external force, the plug post 122 and the plated portion 121 are both bent, thereby ensuring the plug post 122 can open the first opening 1110 when bending.

In addition, in a preferred embodiment, the plated portion 121 may be implemented without the annular recess, and the plug post 122 may be implemented without the necked portion. In other words, the top surface and the bottom surface of the plated portion 121 may be parallel with each other, and the plug post 122 may be a straight cylinder.

The following are still other preferred embodiments.

With reference to FIGS. 1 to 4, the second connecting assembly 20 is detachably connected to the vial B, and communicates with the vial B. The second connecting assembly 20 is detachably connected to the first connecting assembly 10. The second connecting assembly 20 has a second sleeve 21, a connecting portion 22, and a second resilient valve 23, and optionally has a third resilient valve 24.

The second sleeve 21 has a first end, a second end, and a second channel 211. The first end is detachably connected to the vial B, and the second end is detachably connected to the second end of the first sleeve 11. The second channel 211 is formed through the second sleeve 21, extends from the first end to the second end, and communicates with the vial B. The second channel 211 forms a second opening 2110 in the second end of the second sleeve 21. In a preferred embodiment, the second sleeve 21 may have a third sleeve unit 21a and a fourth sleeve unit 21b. The third sleeve unit 21a is detachably connected to the second sleeve unit 11b of the first sleeve 11. The fourth sleeve unit 21b is mounted securely on the third sleeve unit 21a, and is detachably connected to the vial B. In other words, the third sleeve unit 21a forms the first end of the second sleeve 21, and the fourth sleeve unit 21b forms the second end of the second sleeve 21. The second channel 211 is formed through the third sleeve unit 21a and the fourth sleeve unit 21b, and the second opening 2110 is formed in the third sleeve unit 21a.

The connecting portion 22 is mounted in the second channel 211, and in a preferred embodiment, the connecting portion 22 is movably mounted in the second channel 211. The connecting portion 22 has an opening end 221, a closed end 222, and a third channel 223. The third channel 223 is formed in the connecting portion 22, and extends from the opening end 221 to the closed end 222. The closed end 222 of the connecting portion 22 is selectively exposed, and has at least one lateral hole 224. The lateral hole 224 is formed through a side wall of the connecting portion 22 and communicates with the third channel 223. The lateral hole 224 is disposed adjacent to the closed end 222, and thus the lateral hole 224 is selectively exposed out with the closed end 222.

In a preferred embodiment, the connecting portion 22 optionally has a protrusion 225. The protrusion 225 protrudes from the closed end 222 and protrudes along a lengthwise direction of the connecting portion 22.

The second resilient valve 23 is mounted in the second channel 211, and selectively seals the second opening 2110. The second resilient valve 23 has a first sealing portion 231 and a first surrounding portion 232. The first sealing portion 231 is disposed in the second opening 2110 of the second sleeve 21, and a periphery of the first sealing portion 231 selectively seals and abuts the second opening 2110. The first sealing portion 231 has a first resilient opening 2310. The first resilient opening 2310 is selectively mounted around the side wall of the connecting portion 22, or the first resilient opening 2310 is closed itself.

One of two ends of the first surrounding portion 232 is mounted on the first sealing portion 231, and the other end abuts the connecting portion 22. In a preferred embodiment, the first surrounding portion 232 and the first sealing portion 231 are formed integrally. But in another preferred embodiment, the first surrounding portion 232 and the first sealing portion 231 may be two separate components, and the first surrounding portion 232 abuts the first sealing portion 231. The first surrounding portion 232 is made of a resilient material to dispose the first sealing portion 231 in the second opening 2110, so that the first sealing portion 231 seals the second opening 2110 and the first resilient opening 2310 is closed itself.

The third resilient valve 24 is mounted in the second channel 211, and selectively blocks the second channel 211. In a preferred embodiment, the third sleeve unit 21a and the fourth sleeve unit 21b clamp the third resilient valve 24 securely. The third resilient valve 24 has a second sealing portion 241 and optionally has a second surrounding portion 242. The second sealing portion 241 is mounted in the second channel 211, and a periphery of the second sealing portion 241 seals and abuts an inner wall of the second channel 211. The second sealing portion 241 has a second resilient opening 2410. The second resilient opening 2410 is selectively mounted around the connecting portion 22, and can be closed itself to block the second channel 211.

One of two ends of the second surrounding portion 242 is mounted on the second sealing portion 241, and the other end abuts the connecting portion 22. In a preferred embodiment, the second surrounding portion 242 and the second sealing portion 241 are formed integrally. But in another preferred embodiment, the second surrounding portion 242 and the second sealing portion 241 may be two separate units, and the second surrounding portion 242 abuts the second sealing portion 241. The second surrounding portion 242 is made of a resilient material, which makes the closed end 222 of the connecting portion 22 tend to keep adjacent to the second opening 2110 of the second channel 211, and also prevents the connecting portion 22 from mounting through the second sealing portion 241.

Figure 4:
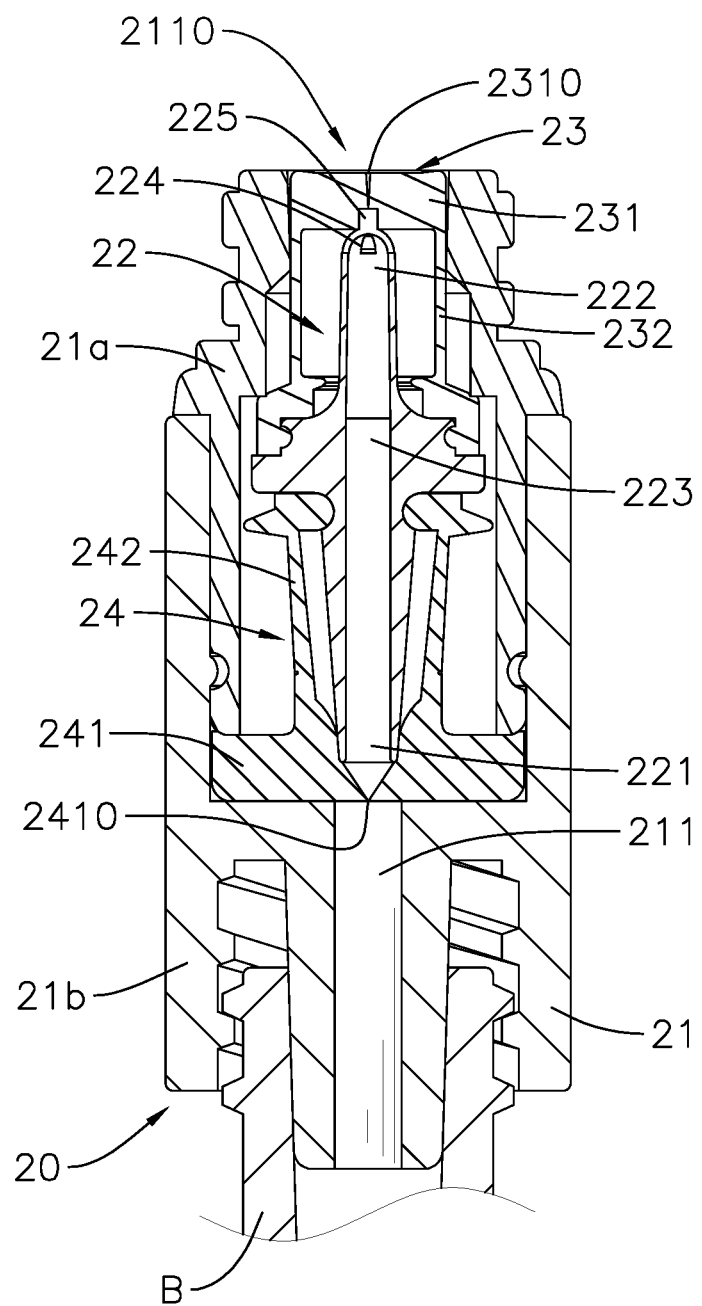
FIGS. 4 and 6 are enlarged views of FIG. 3.
Figure 5:
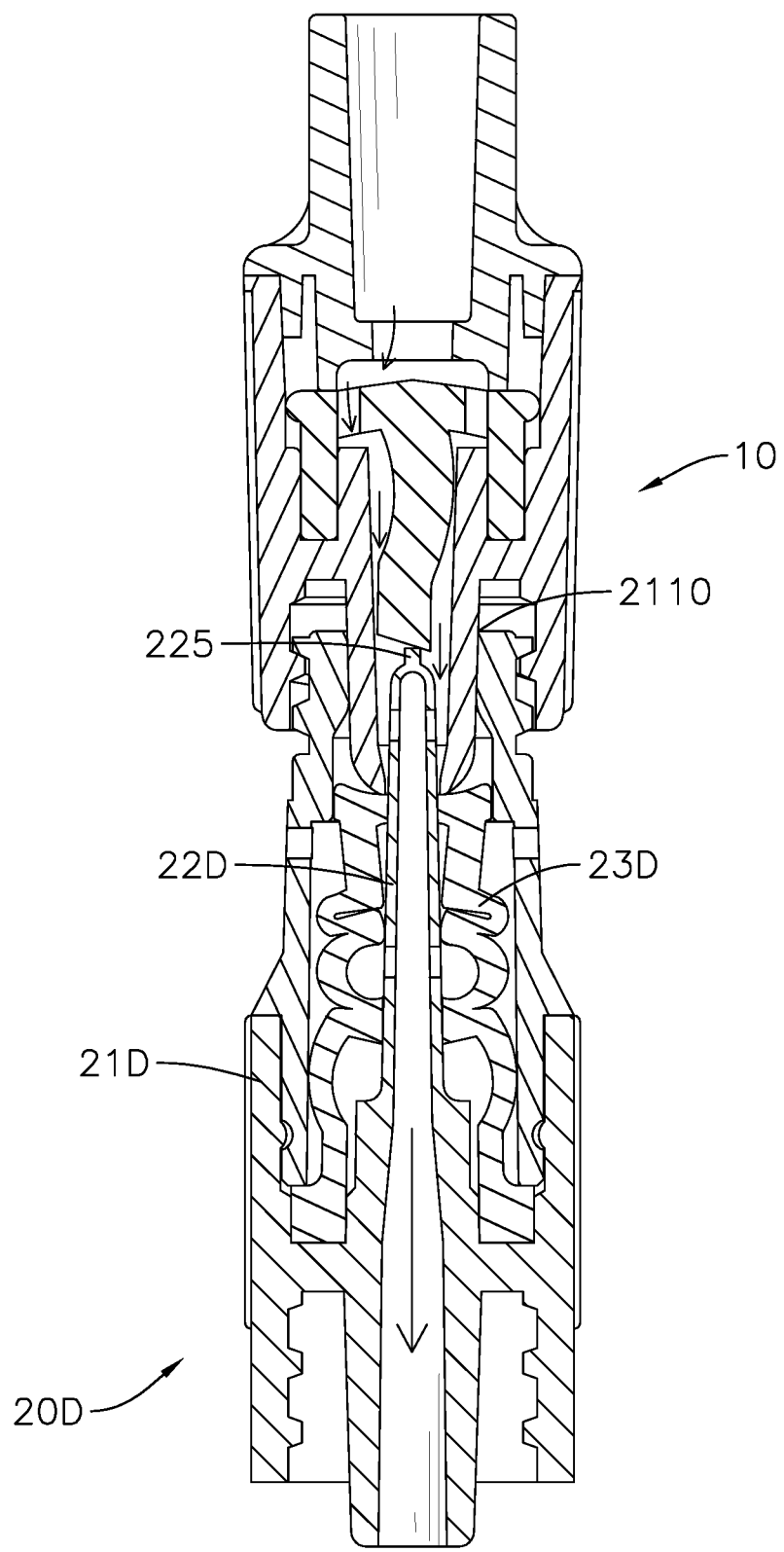
FIG. 5 is a front view in partial section of the second connecting assembly of another embodiment of a body-fluid-and-medication leak-proof and closed medical connector in accordance with the present invention.

With reference to FIG. 5, in still another preferred embodiment, the second connecting assembly 20D is similar to the aforementioned second connecting assembly 20 as shown in FIG. 4. The difference is that the connecting portion 22D is mounted securely in the second sleeve 21D, and thus the connecting portion 22D is unmovable relative to the second sleeve 21D. Besides, the second connecting assembly 20D does not have the third resilient valve, and only has the second resilient valve 23D. The second resilient valve 23D also surrounds the connecting portion 22D and selectively seals the second opening 2110 of the second sleeve 21D, thereby reducing the components of the second connecting assembly 20D to facilitate manufacture.

With the aforementioned structure, when dispensing the medication, separate the first connecting assembly 10 and the second connecting assembly 20 first, and then mount the first connecting assembly 10 on the injector A, and mount the second connecting assembly 20 on the vial B. At this time, the resilience of the first resilient valve 12 makes the plug post 122 of the first resilient valve 12 seal the first opening 1110 of the first sleeve 11, thereby blocking the first channel 111 of the first sleeve 11. As a result, the medication cannot flow into the first connecting assembly 10 from the first opening 1110.

As the same time, the resilience of the second resilient valve 23 makes the first sealing portion 231 of the second resilient valve 23 disposed in the second opening 2110 of the second sleeve 21, and the connecting portion 22 is not mounted through the first resilient opening 2310 of the first sealing portion 231, so that the first resilient opening 2310 is closed, and the medication cannot flow into the second sleeve 21 from the second opening 2110. Simultaneously, the protrusion 225 of the connecting portion 22 points to the first resilient opening 2310 or is mounted in the first resilient opening 2310. But the protrusion 225 does not open the first resilient opening 2310.

On the other hand, the resilience of the third resilient valve 24 makes the second surrounding portion 242 of the third resilient valve 24 abut against the connecting portion 22, so that the closed end 222 of the connecting portion 22 tends to keep adjacent to the second opening 2110 of the second channel 211, and also prevents the connecting portion 22 from mounting through the second resilient opening 2410 of the second sealing portion 241 of the third resilient valve 24. As a result, the second resilient opening 2410 is closed, and the medication cannot pass through the third resilient valve 24.

Then, connect the first connecting assembly 10 and the second connecting assembly 20, which makes the first sleeve 11 abut the second resilient valve 23. The first sleeve 11 may abut the second resilient valve 23 in various manners. For example, the first sleeve 11 pushes the first sealing portion 231 of the second resilient valve 23 via the side wall of the first channel 111, thereby pressing the first surrounding portion 232 of the second resilient valve 23 to be deformed. Therefore, the first sealing portion 231 moves along the connecting portion 22, opens the first resilient opening 2310, and moves downward along the connecting portion 22, which exposes the closed end 222 and the lateral hole 224 of the connecting portion 22 out of the first sealing portion 231. Besides, the protrusion 225 also facilitates mounting the connecting portion 22 through the first resilient opening 2310.

In a preferred embodiment that the connecting portion 22 is moveable, the connecting portion 22 is abutted against the second resilient valve 23 and the third resilient valve 24 simultaneously. Thus, when the first sleeve 11 abuts the second resilient valve 23, the second resilient valve 23 abuts the connecting portion 22, and the connecting portion 22 abuts the third resilient valve 24, so that the third resilient valve 24 is deformed, and the connecting portion 22 moves toward the vial B. To be specific, the connecting portion 22 moves until the opening end 221 of the connecting portion 22 is mounted through the second resilient opening 2410, thereby the second channel 211 and the third channel 223 communicating with each other.

On the other hand, when the first connecting assembly 10 and the second connecting assembly 20 are connected to each other, the exposed connecting portion 22 will mount through the first opening 1110 and into the first channel 111 of the first sleeve 11, and abut the first resilient valve 12, so that the first resilient valve 12 is deformed and open the first opening 1110. To be specific, when the connecting portion 22 is mounted into the first channel 111, the connecting portion 22 abuts the first resilient valve 12 via the protrusion 225, which makes the first resilient valve 12 deformed and then open the first opening 1110. For example, as in the aforementioned first preferred embodiment, the plug post 122 of the first resilient valve 12 can be deformed by the abutting of the connecting portion 22. So the first opening 1110 still can be opened even though the plated portion 121 of the first resilient valve 12 stays in the original position. Or as in the aforementioned fourth preferred embodiment, the flexing portion 124B of the first resilient valve 12 can be deformed by the abutment of the connecting portion 22 against the plug post 122, which makes the plug post 122 move toward the injector A and open the first opening 1110. When the first opening 1110 is opened, the first channel 111 and the third channel 223 communicate with each other.

At this time, the first channel 111, the second channel 211, and the third channel 223 communicate with each other, so that the medication in the vial B can flow into the second channel 211, the third channel 223, the first channel 111, and finally into the injector A in sequence.

When finishing the transfer of the medication, separate the first connecting assembly 10 and the second connecting assembly 20. During the separating, the side wall of the first channel 111 gradually moves out of the second channel 211, and the first sealing portion 231 of the second resilient valve 23 moves toward the first connecting assembly 10 and keeps abutting against an edge of the first opening 1110 of the first channel 111. Simultaneously, the connecting portion 22 keeps staying in the first resilient opening 2310 of the first sealing portion 231. As a result, a gap between the first channel 111 and the second channel 211 will not expand during the separating.

When the first connecting assembly 10 and the second connecting assembly 20 further separate, the first sealing portion 231 keeps moving toward the first connecting assembly 10 and covers the lateral hole 224 of the connecting portion 22, thereby isolating the first channel 111 and the third channel 223. Afterwards, the first sealing portion 231 covers the protrusion 225 to stop the protrusion 225 abutting the plug post 122. At this time, the connecting portion 22 is fully covered by the first sealing portion 231, and the first resilient opening 2310 is fully closed. The first resilient valve 12 does not receive any external force and then is recovered to seal the first opening 1110.

Afterwards, when the side wall of the first channel 111 is moving out of the second channel 211, the first sealing portion 231 keeps moving toward the second opening 2110. When the side wall of the first channel 111 fully moves out of the second channel 211, the first sealing portion 231 also moves to the second opening 2110 and seals the second opening 2110. At this time, the first connecting assembly 10 and the second connecting assembly 20 are fully separated. As a result, the medication remaining in the first sleeve 11 will not flow out of the first opening 1110, and there will be no medication remaining outside of the first sleeve 11. At the same time, the third resilient valve 24 is recovered and blocks the second channel 211, thereby strengthening the closing of the inner side of the second connecting assembly 20, which prevents the medication from flowing back to the second sleeve 21 from the vial B.

As a result, during the separating of the first connecting assembly 10 and the second connecting assembly 20, the first sealing portion 231 will cover the lateral hole 224 first, which prevents the medication from flowing into the first channel 111 via the lateral hole 224. Then, the first sealing portion 231 covers the protrusion 225, and the protrusion 225 and the first resilient valve 12 are separated, which makes the first resilient valve 12 seal the first opening 1110, so that the medication will not flow back to the second connecting assembly 20 from the first opening 1110. During the subsequent separating, the first sealing portion 231 keeps abutting against the side wall of the first channel 111, so that no gap will be formed between the first sealing portion 231 and the first opening 1110 to accommodate medication. As a result, when the first connecting assembly 10 and the second connecting assembly 20 are fully separated, the first sealing portion 231 will immediately seal the second opening 2110, thereby avoiding medication remaining in the first opening 1110 and the second opening 2110.

Figure 12:
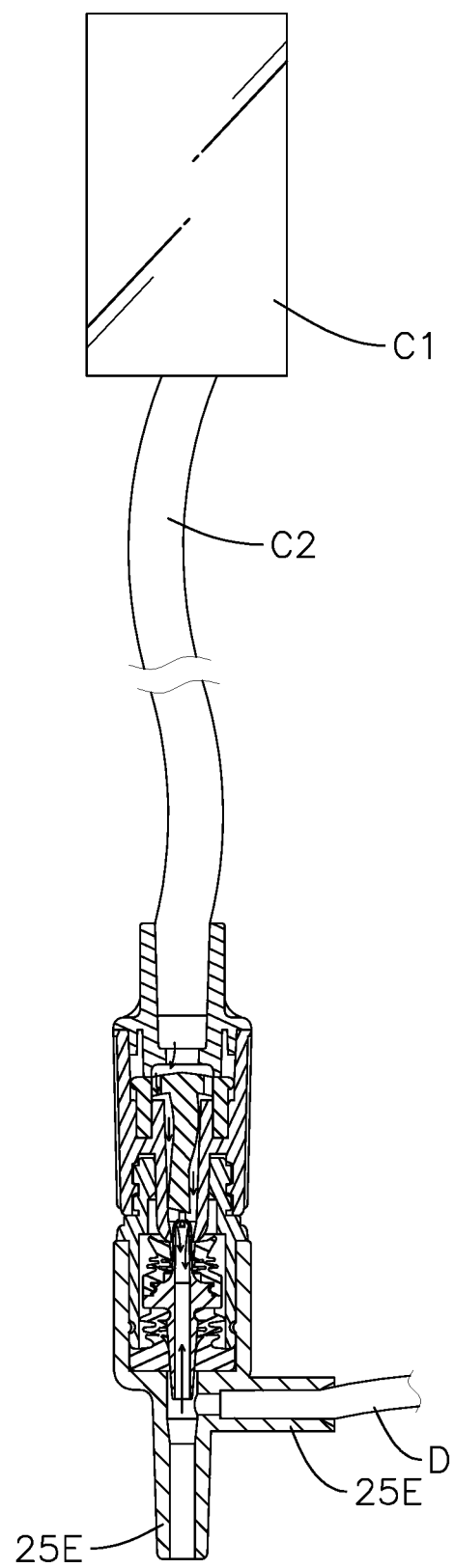
FIG. 12 is a front view in partial section of the body-fluid-and-medication leak-proof and closed medical connector in FIG. 1, shown connected to a fluid infusion tube.
Figure 13:
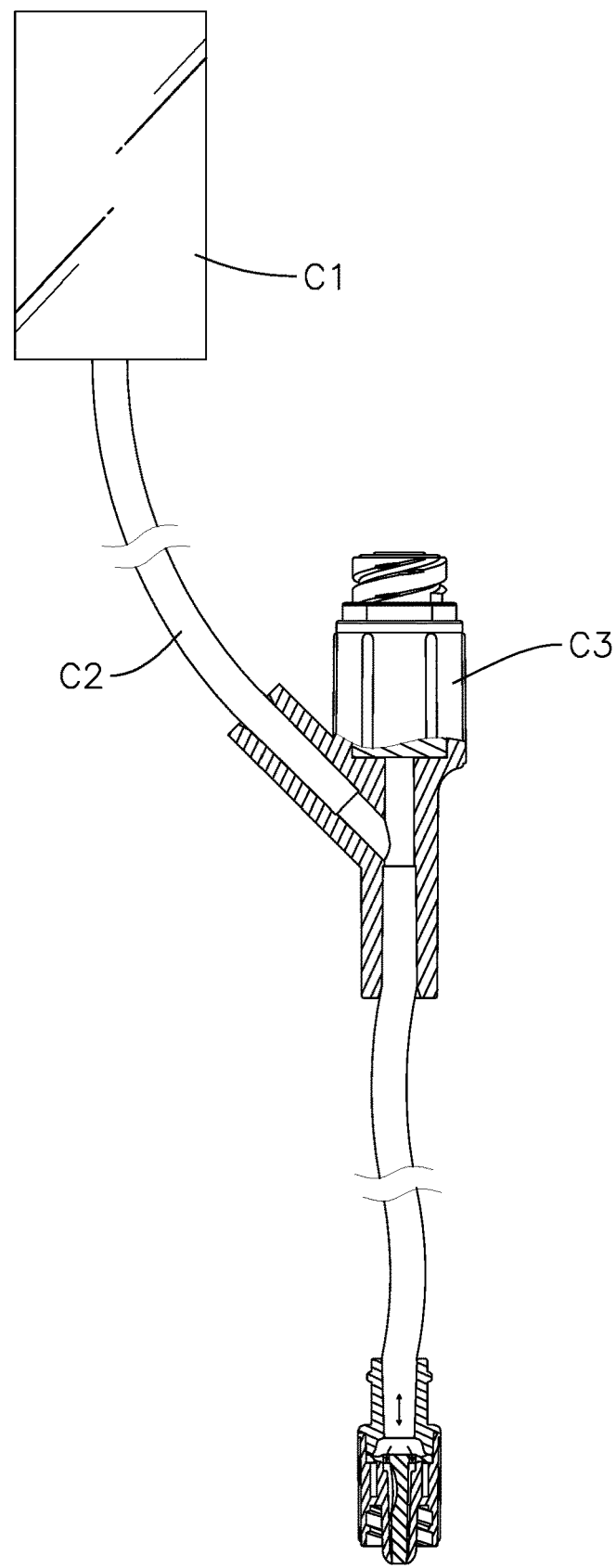
FIG. 13 is a front view in partial section of the body-fluid-and-medication leak-proof and closed medical connector in FIG. 1, shown connected to a diverter.

With reference to FIGS. 12 and 13, the present invention not only can connect the injector and the vial, but also can connect a fluid infusion bag C1 and a human body. To be specific, two ends of a fluid infusion tube C2 are respectively connected to the fluid infusion bag C1 and the first connecting assembly 10, thereby communicating between the fluid infusion bag C1 and the first connecting assembly 10. Similarly, one of two ends of a catheter D is installed with a needle (not shown in the drawings), and the other end is connected to the second connecting assembly 20. The catheter D is for connecting to a human body. The fluid infusion tube C2 can directly communicate with the fluid infusion bag C1 and the first connecting assembly 10 as shown in FIG. 12, or the fluid infusion tube C2 can be connected to the fluid infusion bag C1 via a diverter C3 as shown in FIG. 13 to receive two kinds of the medications. In addition, if the second connecting assembly 20 is not connected to the vial, a bottom end of the second connecting assembly 20 can be formed with one single or multiple tube-connecting portions 25E to simultaneously connect to multiple catheters D as shown in FIG. 12 rather than formed with threads for the vial B as shown in FIG. 1.

To sum up, two ends of the present invention can be respectively connected to an injector A and a vial B, so that the medication in the vial B can flow into the injector A via the present invention. In addition, after transferring the medication, the first connecting assembly 10 and the second connecting assembly 20 of the present invention can be separated. The first resilient valve 12 in the first sleeve 11 of the first connecting assembly 10 tends to seal the first opening 1110 of the first sleeve 11, thereby avoiding the leakage of the medication remaining in the first connecting assembly 10. At the same time, the second resilient valve 23 in the second sleeve 21 of the second connecting assembly 20 tends to seal the second opening 2110, thereby avoiding the leakage of the medication remaining in the second connecting assembly 20.

The aforementioned means of sealing, i.e. sealing the first opening 1110 first and then sealing the second opening 2110, can effectively reduce the contact between the medication and the air, and also reduce the medication remaining on outer surfaces of the first connecting assembly and the second connecting assembly to prevent the remaining medication contacting the human body. Therefore, the transfer of the medication is more hygienic and safe. In addition, by reducing the medication remaining outside of the vial, the user can draw appropriate dose of precious chemotherapy medication from the vial, thereby effectively reducing waste of medical resources.

Figure 14:
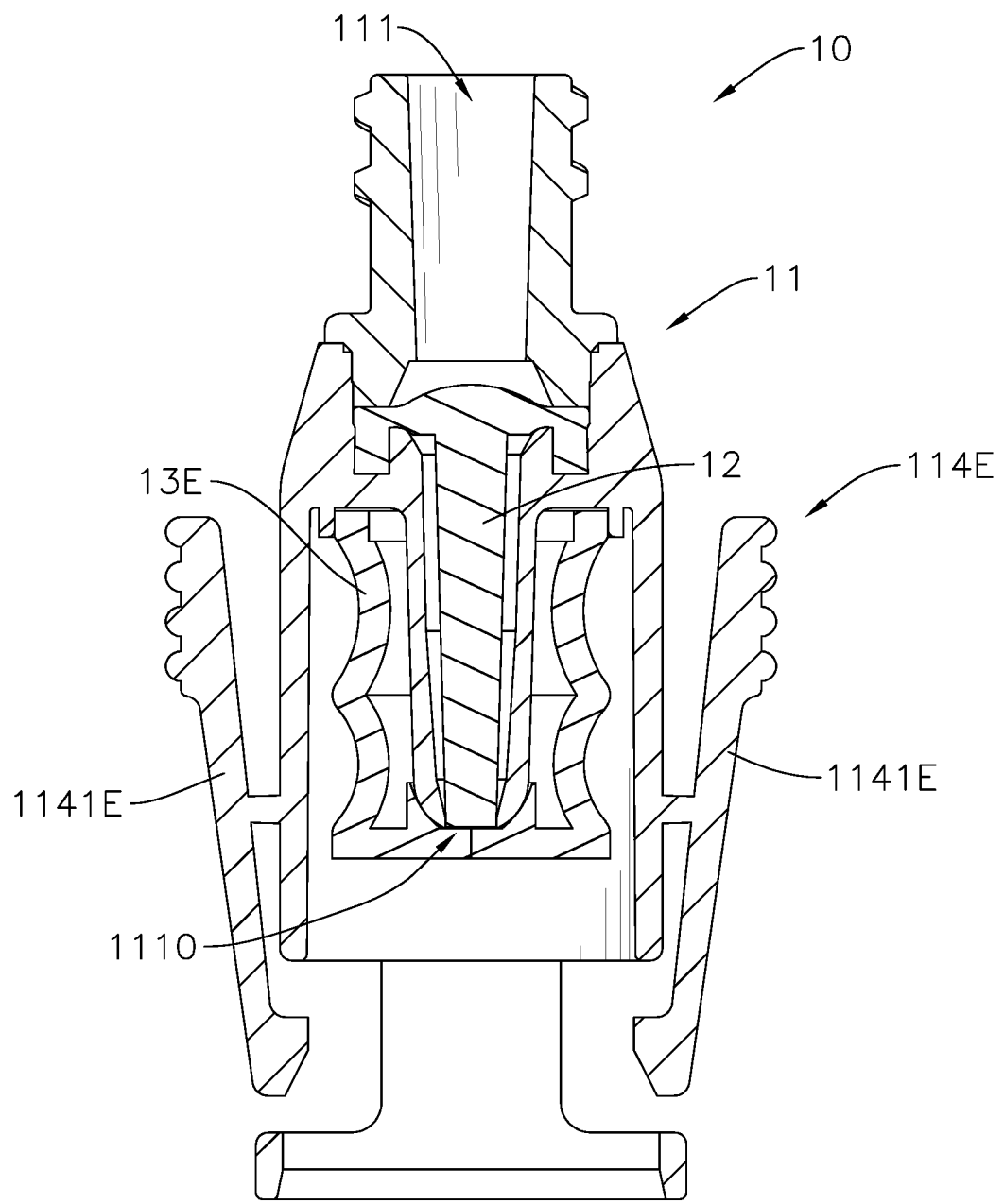
FIG. 14 is a front view in partial section of the first connecting assembly of a fifth embodiment of a body-fluid-and-medication leak-proof and closed medical connector in accordance with the present invention.
Figure 15:
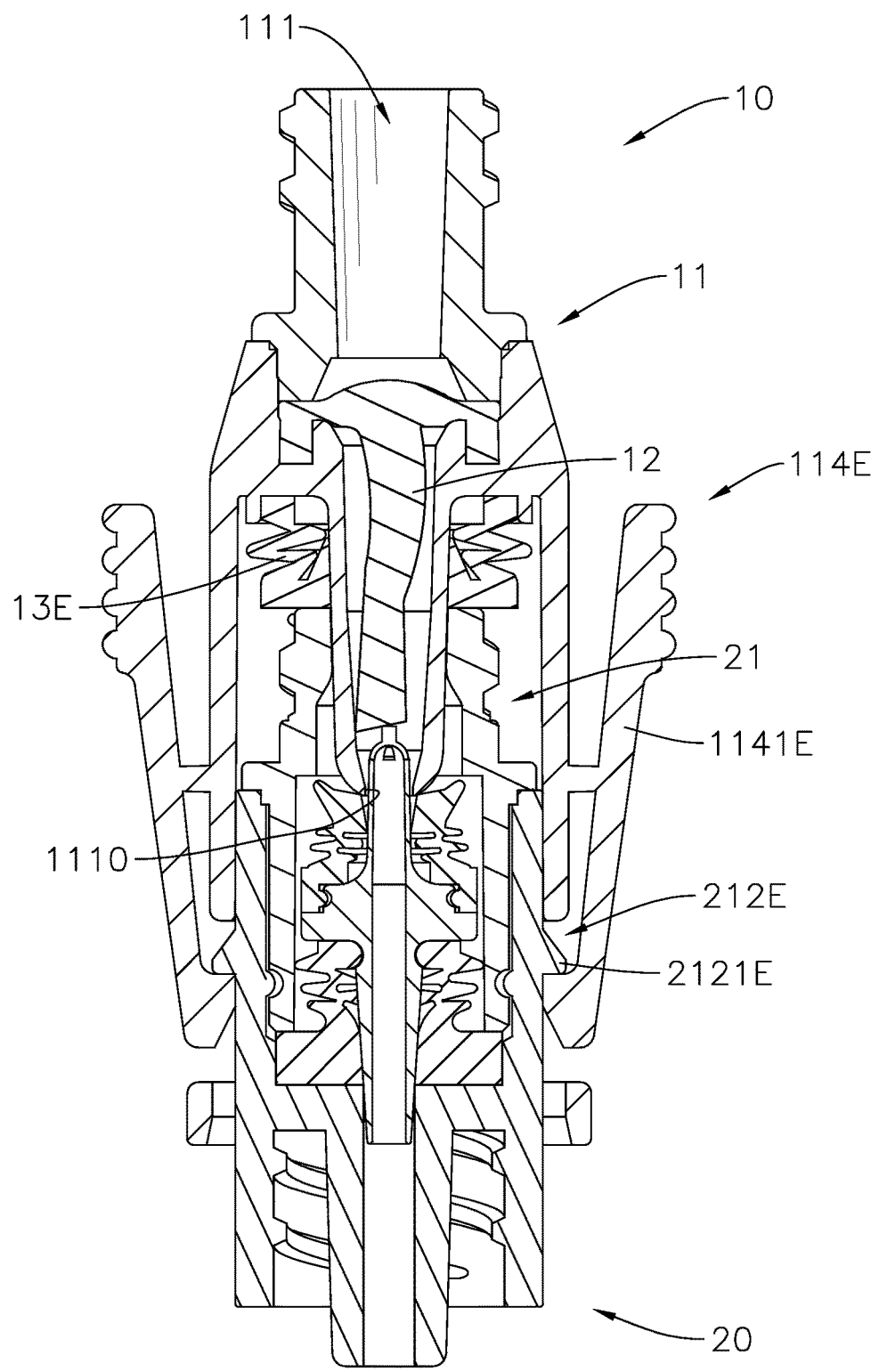
FIG. 15 is a front view in partial section of the body-fluid-and-medication leak-proof and closed medical connector in FIG. 14, showing the first connecting assembly and the second connecting assembly connected with each other.

In addition, a fifth embodiment as shown in FIGS. 14 and 15 is similar to the aforementioned first embodiment, but there are two differences between the two embodiments.

First, in the first embodiment, the first connecting assembly 10 and the second connecting assembly 20 are connected with each other by threads. But in the fifth embodiment, the first connecting assembly 10 and the second connecting assembly 20 are connected by engaging without rotating. To be precise, the first sleeve 11 further has a first engaging portion 114E formed on an outer surface of the first sleeve 11. The second sleeve 21 further has a second engaging portion 212E formed on an outer surface of the second sleeve 21. The second engaging portion 212E selectively engages with the first engaging portion 114E to connect the first connecting assembly 10 and the second connecting assembly 20. That is, the first connecting assembly 10 can be moved toward the second connecting assembly 20 until the engaging portion 114E engages with the second engaging portion 212E, which fixes and prevents the first connecting assembly 10 and the second connecting assembly 20 from separating.

In a preferred embodiment, the first engaging portion 114E comprises multiple engaging hooks 1141E connected to the outer surface of the first sleeve 11. Each one of the engaging hooks 1141E is elongated, and two opposite ends of the engaging hook 1141E are respectively a pressing end and an engaging end. The engaging end is proximal to the second connecting assembly 20 relative to the pressing end. When the pressing end is pressed, the engaging end will be lifted up. The second engaging portion 212E comprises an annular flange 2121E formed on the outer surface of the second sleeve 21. The annular flange 2121E selectively engages with the engaging ends of the engaging hooks 1141E.

When the first connecting assembly 10 is moved toward the second connecting assembly 20, the engaging ends of the engaging hooks 1141E may be pushed outward by the annular flange 2121E due to slopes of the annular flange 2121E and the engaging ends. After passing the annular flange 2121E, the engaging hooks 1141E is recovered and engage a bottom periphery of the annular flange 2121E. To separate the first connecting assembly 10 and the second connecting assembly 20, just press the pressing ends of the engaging hooks 1141E, and then the first connecting assembly 10 can be moved upward from the second connecting assembly 20.

However, the first engaging portion 114E and the second engaging portion 212E may be implemented with other structures or shapes.

Second, in the fifth embodiment, the first connecting assembly 10 further comprises a fourth resilient valve 13E. The fourth resilient valve 13E surrounds the first channel 111, selectively wraps around the second end of the first sleeve 11 to seal the first opening 1110. When the first connecting assembly 10 and the second connecting assembly 20 are connected to each other, the second end of the second sleeve 21 abuts the fourth resilient valve 13E to move the fourth resilient valve 13E relative to the first sleeve 11 to expose the first opening 1110 out of the fourth resilient valve 13E.

Therefore, the first opening 1110 is not only sealed by the block of the first resilient valve 12 from the inside of the first channel 111, but also sealed by the wrapping of the fourth resilient valve 13E, which further strengthens the sealing of the first opening 1110.

Figure 16:
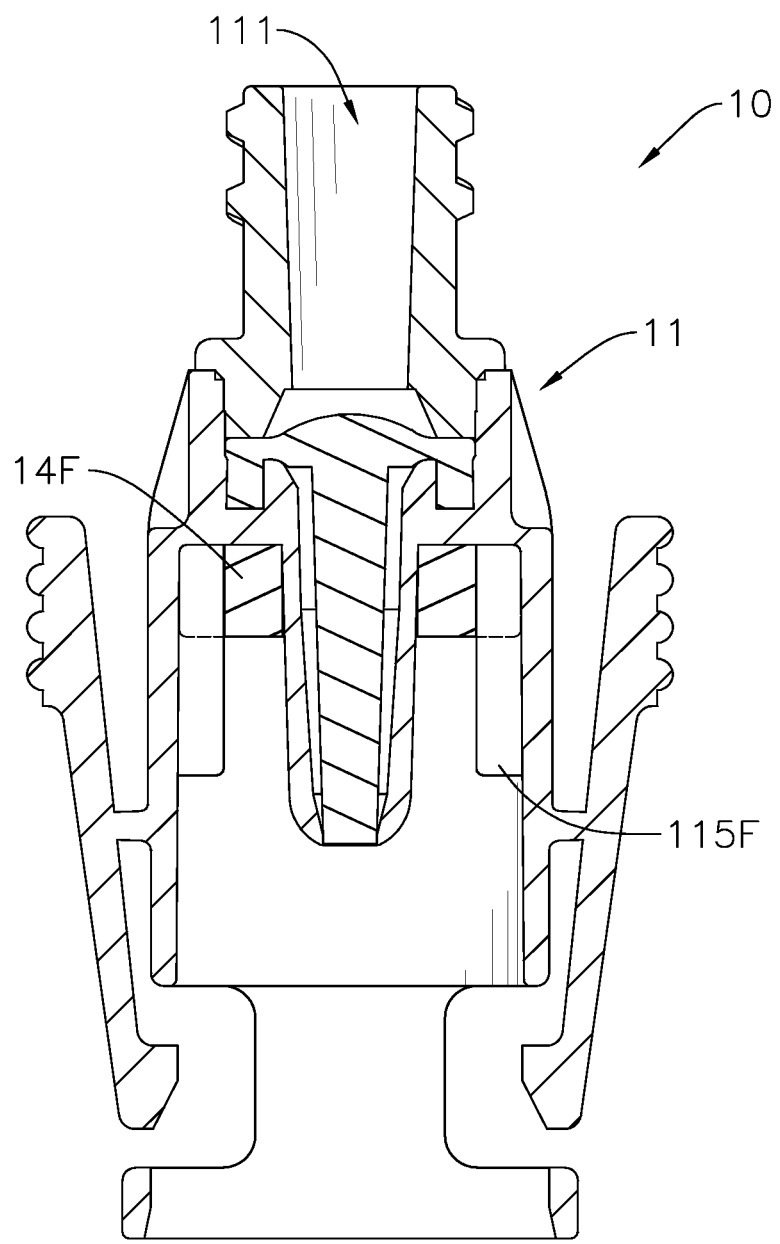
FIG. 16 is a front view in partial section of the first connecting assembly of a sixth embodiment of a body-fluid-and-medication leak-proof and closed medical connector in accordance with the present invention.
Figure 17:
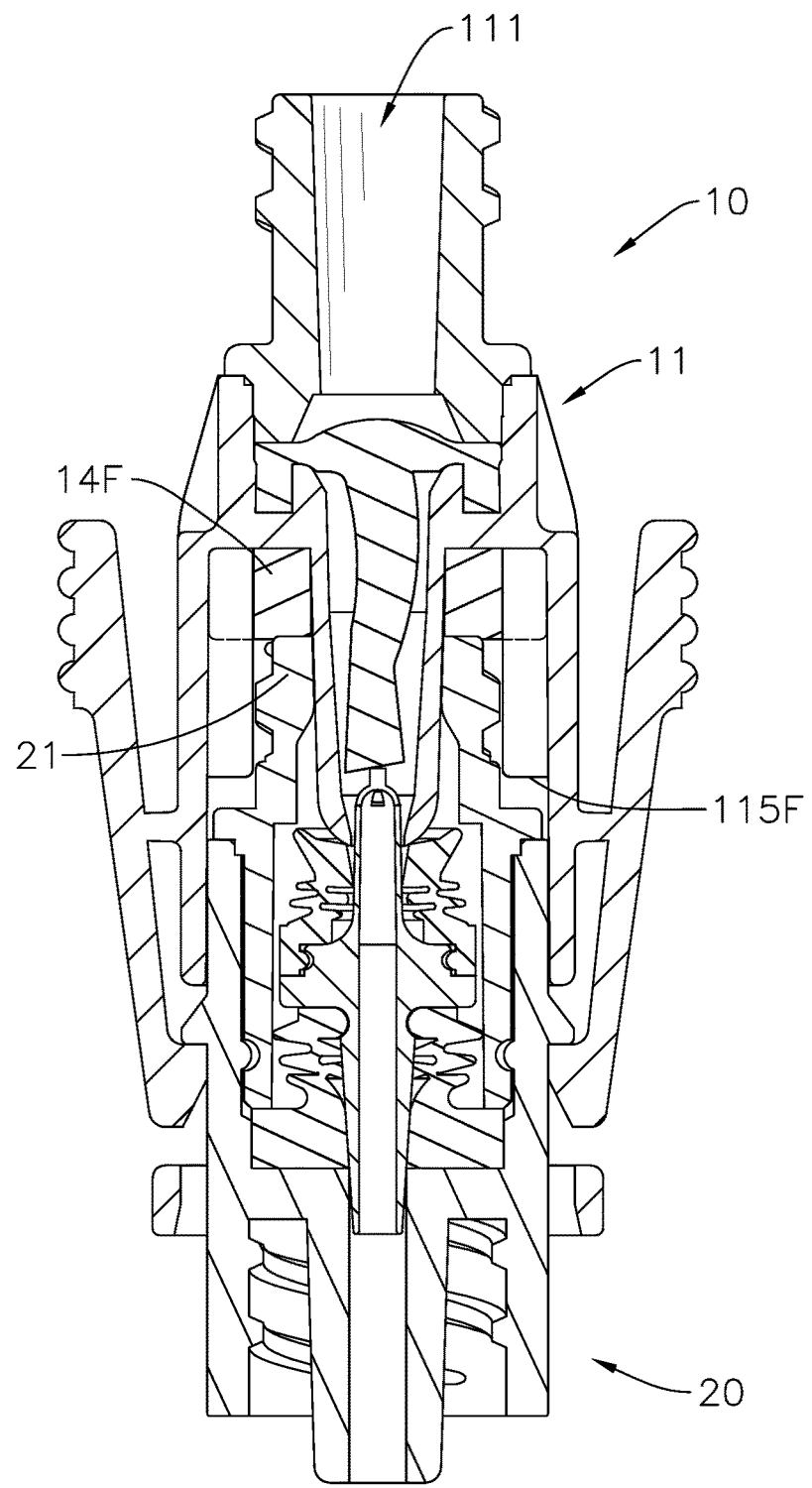
FIG. 17 is a front view in partial section of the body-fluid-and-medication leak-proof and closed medical connector in FIG. 16, showing the first connecting assembly and the second connecting assembly connected with each other.
Figure 18:
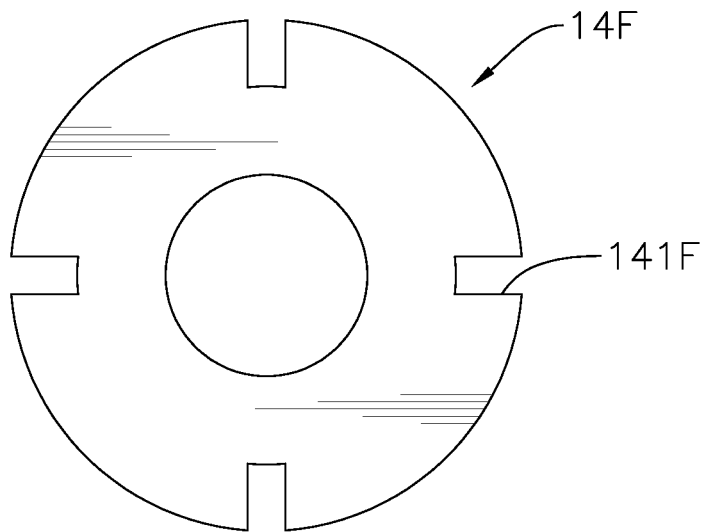
FIG. 18 is a top view of a resilient spacer of the body-fluid-and-medication leak-proof and closed medical connector in FIG. 16.

In addition, a sixth embodiment as shown in FIGS. 16 to 17 is similar to the aforementioned fifth embodiment, but there is a difference between the two embodiments.

The sixth embodiment has no fourth resilient valve 13E but has a resilient spacer 14F instead. The resilient spacer 14F surrounds the first channel 111 and abuts the first sleeve 11 toward the first end of the first sleeve 11. When the first connecting assembly 10 and the second connecting assembly 20 are connected to each other, the second end of the second sleeve 21 abuts against the resilient spacer 14F, and the resilient spacer 14F is clamped between the second sleeve 21 and the first sleeve 11 along a lengthwise direction of the first channel 111, thereby strengthening the sealing of infusion and toxic gas from hazardous drugs, completely prevent leakage during using.

In a preferred embodiment, the first sleeve 11 further has multiple fixing ribs 115F formed on an inner wall of the first sleeve 11. The resilient spacer 14F further has multiple fixing recesses 141F formed in an annular wall of the resilient spacer 14F. The fixing recesses 141F respectively engage with the fixing ribs 115F of the first sleeve 11, so that the resilient spacer 14F is mounted on the first sleeve 11. But the resilient spacer 14F may be connected to the first sleeve 11 by other structure.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A body-fluid-and-medication leak-proof and closed medical connector, one of two ends of the body-fluid-and-medication leak-proof and closed medical connector detachably connected to an injector or a fluid infusion tube, the other of the two ends of the body-fluid-and-medication leak-proof and closed medical connector detachably connected to a vial or a catheter, thereby communicating between the injector and the vial, or communicating between the fluid infusion tube and the catheter; the body-fluid-and-medication leak-proof and closed medical connector comprising:

a first connecting assembly detachably connected to an injector or a fluid infusion tube, communicating with the injector or the fluid infusion tube, and comprising a first sleeve having
   a first end detachably connected to the injector or the fluid infusion tube;
   a second end; and
   a first channel formed through the first sleeve, extending from the first end of the first sleeve to the second end of the first sleeve, communicating with the injector or the fluid infusion tube, and forming a first opening in the second end of the first sleeve; and
a first resilient valve mounted in the first channel and selectively sealing the first opening; the first resilient valve comprising:
   a plated portion having
     multiple communicating holes formed through the plated portion between two ends of the first channel; and
   a plug post mounted securely on the plated portion, selectively sealing the first opening, a length of the plug post being larger than a width of the plug post, and the plug post having a necked portion between two ends of the plug post; and
a second connecting assembly detachably connected to a vial or a catheter, communicating with the vial or the catheter, detachably connected to the first connecting assembly, and comprising
a second sleeve having
   a first end detachably connected to the vial or the catheter;
   a second end detachably connected to the second end of the first sleeve; and
   a second channel formed through the second sleeve, extending from the first end of the second sleeve to the second end of the second sleeve, communicating with the vial or the catheter, and forming a second opening in the second end of the second sleeve;
a connecting portion mounted in the second channel and having
   a closed end; and
   at least one lateral hole formed through a side wall of the connecting portion, communicating with an inner space of the connecting portion, and disposed adjacent to the closed end of the connecting portion; and
a second resilient valve mounted in the second channel, and selectively sealing the second opening;
wherein when the first connecting assembly and the second connecting assembly are connected to each other, the first sleeve abuts the second resilient valve to move the second resilient valve relative to the connecting portion to expose the at least one lateral hole of the connecting portion out of the second resilient valve; simultaneously, the closed end of the connecting portion abuts the first resilient valve to open the first opening such that the first connecting assembly and the second connecting assembly communicate with each other; the plug post is made of a resilient material and thus is bent due to the necked portion abutting against the connecting portion and thereby the first opening is opened.

2. The body-fluid-and-medication leak-proof and closed medical connector as claimed in claim 1, wherein the connecting portion further comprises
   a protrusion protruding from the closed end of the connecting portion, and protruding along a lengthwise direction of the connecting portion.

3. The body-fluid-and-medication leak-proof and closed medical connector as claimed in claim 1, wherein the necked portion has a notch formed in a side surface of the plug post.

4. The body-fluid-and-medication leak-proof and closed medical connector as claimed in claim 1, wherein
the first sleeve has
   a positioning recess surrounding the first channel; and
the first resilient valve has
   a positioning portion surrounding the plug post, one of two ends of the positioning portion connected to the plated portion, and the other of the two ends of the positioning portion mounted in the positioning recess.

5. The body-fluid-and-medication leak-proof and closed medical connector as claimed in claim 4, wherein
the positioning recess extends along a direction perpendicular to a lengthwise direction of the first channel; and
the positioning portion has
   an extending wall shaped as a sleeve and surrounding the plug post; one of two ends of the extending wall connected to the plated portion; and
   a protruding rib extending from the other end of the extending wall along a direction perpendicular to the lengthwise direction of the first channel.

6. The body-fluid-and-medication leak-proof and closed medical connector as claimed in claim 1, wherein the second connecting assembly further comprises
   a third resilient valve mounted in the second channel, and selectively blocking the second channel;
wherein when the first connecting assembly and the second connecting assembly are connected to each other, the connecting portion of the second connecting assembly abuts the third resilient valve to make the third resilient valve stop blocking the second channel.

\* \* \* \* \*